US012308129B2

(12) United States Patent
Gilbert et al.

(10) Patent No.: US 12,308,129 B2
(45) Date of Patent: May 20, 2025

(54) ACCESS TO MULTIPLE CAREGIVER INFORMATION SYSTEMS

(71) Applicant: Hill-Rom Services, Inc., Batesville, IN (US)

(72) Inventors: Jeffrey A. Gilbert, Saint Petersburg, FL (US); Justin Haldane, Tampa, FL (US)

(73) Assignee: Hill-Rom Services, Inc., Batesville, IN (US)

( * ) Notice: Subject to any disclaimer, the term of this patent is extended or adjusted under 35 U.S.C. 154(b) by 311 days.

(21) Appl. No.: 17/453,246

(22) Filed: Nov. 2, 2021

(65) Prior Publication Data

US 2022/0139569 A1     May 5, 2022

Related U.S. Application Data

(60) Provisional application No. 63/109,499, filed on Nov. 4, 2020.

(51) Int. Cl.
*G16H 40/20* (2018.01)
*G16H 40/63* (2018.01)
*G16H 80/00* (2018.01)

(52) U.S. Cl.
CPC .............. *G16H 80/00* (2018.01); *G16H 40/20* (2018.01); *G16H 40/63* (2018.01)

(58) Field of Classification Search
CPC ........ G16H 80/00; G16H 40/20; G16H 40/63; G16H 40/67; G06Q 10/10; H04W 4/08; H04L 67/12
USPC ....................................................... 705/2–3
See application file for complete search history.

(56) References Cited

U.S. PATENT DOCUMENTS

| | | | |
|---|---|---|---|
| 9,058,635 | B1 | 6/2015 | Rybkin |
| 9,652,593 | B1 * | 5/2017 | Schoenberg ............ H04L 67/54 |
| 10,580,279 | B2 | 3/2020 | Herbst et al. |
| 10,667,764 | B2 | 6/2020 | Ahmed et al. |
| 2006/0004588 | A1 * | 1/2006 | Ananda .................. G06Q 10/00 705/67 |
| 2007/0180047 | A1 * | 8/2007 | Dong ..................... A61B 5/117 600/300 |

(Continued)

FOREIGN PATENT DOCUMENTS

| | | |
|---|---|---|
| EP | 3 467 839 A1 | 4/2019 |
| WO | 2014/143151 A1 | 9/2014 |

OTHER PUBLICATIONS

Rodriguez, Location-aware access to hospital information and services, 2004, IEEE Trans Inf Technol Biomed, Dec;8(4):448-55 (Year: 2004).*

(Continued)

*Primary Examiner* — Kambiz Abdi
*Assistant Examiner* — Tran N Nguyen
(74) *Attorney, Agent, or Firm* — Merchant & Gould P.C.

(57) ABSTRACT

An electronic device for managing notifications for a caregiver associated with multiple healthcare facilities is described. The electronic device connects to an active site associated with a first healthcare facility, connects to a passive site associated with a second healthcare facility, receives the notifications from both the active site and the passive site, and switches the passive site to active upon receipt of an input from the caregiver to access the notifications from the passive site.

16 Claims, 10 Drawing Sheets

(56) References Cited

U.S. PATENT DOCUMENTS

| | | | |
|---|---|---|---|
| 2008/0068447 A1* | 3/2008 | Mattila | H04N 7/15 |
| | | | 348/E7.083 |
| 2008/0221931 A1* | 9/2008 | Schmidt | G16H 30/20 |
| | | | 705/3 |
| 2009/0018872 A1* | 1/2009 | Siepser | G06Q 30/012 |
| | | | 705/2 |
| 2010/0001838 A1* | 1/2010 | Miodownik | G06Q 10/06 |
| | | | 340/10.1 |
| 2011/0153754 A1* | 6/2011 | Gunasekara | G10L 13/00 |
| | | | 704/260 |
| 2012/0290311 A1* | 11/2012 | Tara | G16H 40/20 |
| | | | 705/2 |
| 2013/0066784 A1* | 3/2013 | Dala | G06F 21/6245 |
| | | | 705/51 |
| 2013/0237770 A1* | 9/2013 | Sullivan | A61B 5/021 |
| | | | 600/300 |
| 2013/0325503 A1 | 12/2013 | Abrahams et al. | |
| 2014/0181302 A1* | 6/2014 | Sahoo | H04L 67/303 |
| | | | 709/225 |
| 2014/0282016 A1 | 9/2014 | Hosier, Jr. | |
| 2016/0306930 A1* | 10/2016 | Zavaleta | G16H 10/60 |
| 2017/0004273 A1 | 1/2017 | Mbanefo et al. | |
| 2019/0108908 A1 | 4/2019 | Faulks et al. | |
| 2020/0066401 A1 | 2/2020 | Guelich et al. | |
| 2020/0211360 A1 | 7/2020 | Baker et al. | |

OTHER PUBLICATIONS

Chawasemerwa, Development of a Doctor Scheduling System: A Constraint Satisfaction and Penalty Minimisation Scheduling Model, 2018, Int. J. Res. Ind. Eng. vol. 7, No. 4 396â422 (Year: 2018).*

Moustafa, Remote Monitoring and Medical Devices Control in eHealth, 2016, 2016 IEEE 12th International Conference on Wireless and Mobile Computing, Networking and Communications (WiMob) (Year: 2016).*

Extended European Search Report for Application No. 21206057.8 mailed Mar. 22, 2022.

"Close information gaps and ensure caregiver continuity." Primary Systems Communication & Safety Solutions, 2018.

"Communicate With Confidence." Mobile Heartbeat, www.mobileheartbeat.com, 2020.

* cited by examiner

ACCESS TO MULTIPLE CAREGIVER INFORMATION SYSTEMS

BACKGROUND

Caregivers, such as doctors, nurses, trained medical professions, and the like are typically assigned to multiple patients during a shift in a healthcare facility such as a hospital. Various alerts or calls from patients and other caregivers are communicated to the caregivers who must prioritize and manage the incoming alerts. Other staff members such as those in housekeeping, food service, and patient transporting must also respond to various alerts and calls.

Sometimes caregivers and staff are provided with wireless communication devices, such as pagers or mobile phones, to receive incoming calls and alerts related to the care of one or more patients. At the end of their shift, the caregivers and staff must return these devices such as for recharging or for use by other caregivers and staff on subsequent shifts. More recently, it is common for caregivers and staff to bring their own mobile phones to work to communicate with each other during a shift for purposes of coordinating patient care.

SUMMARY

In general terms, the present disclosure relates to a mobile application that allows a caregiver to access notifications and other resources from multiple healthcare facilities. Various aspects are described in this disclosure, which include, but are not limited to, the following aspects.

In one aspect, an electronic device for managing notifications for a caregiver associated with multiple healthcare facilities includes: a processor; and memory encoding instructions which, when executed by the processor, cause the processor to: connect to an active site associated with a first healthcare facility; connect to a passive site associated with a second healthcare facility; receive notifications from both the active site and the passive site; and switch the passive site to active upon receipt of input from the caregiver to access the passive site.

In another aspect, a method of managing notifications for a caregiver associated with multiple healthcare facilities includes: connecting to an active site associated with a first healthcare facility; connecting to a passive site associated with a second healthcare facility; receiving notifications from both the active site and the passive site; and switching the passive site to active upon receipt of input from the caregiver to access the passive site.

In another aspect, a non-transitory computer readable storage media include computer readable instructions which, when read and executed by a computing device, cause the computing device to: connect to an active site associated with a first healthcare facility; connect to a passive site associated with a second healthcare facility; receive notifications from both the active site and the passive site; and switch the passive site to active upon receipt of input from a caregiver to access the passive site.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
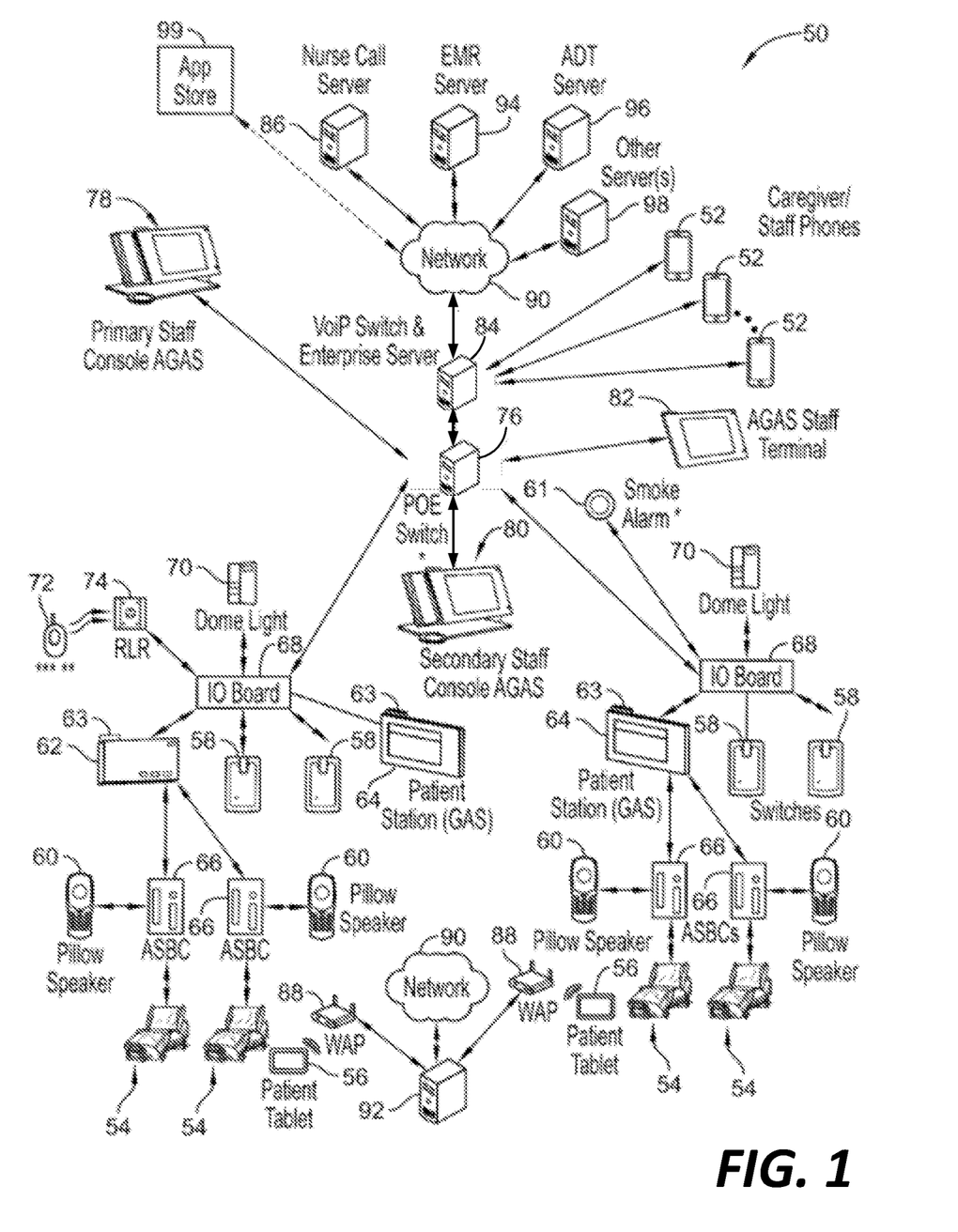
FIG. 1 is a schematic diagram of a caregiver communications system that includes a plurality of mobile phones each equipped with a mobile caregiver application for managing notifications between caregivers in a healthcare facility.

FIG. 1 is a schematic diagram of a caregiver communications system 50 that includes a number of mobile devices 52 that operate a mobile caregiver application 300 (shown in FIG. 3) for managing messages between caregivers and calls and alerts originating from assigned patients and various hospital equipment associated with the assigned patients.

The caregiver communications system 50 is similar to one described in U.S. patent application Ser. No. 16/143,971, titled CAREGIVER AND STAFF INFORMATION SYSTEM, filed on Sep. 27, 2018, the entirety of which is hereby incorporated by reference.

The caregiver communications system 50 and the mobile caregiver application 300 can allow a caregiver to perform functions associated with providing care to patients. This can include logging into the caregiver communications system 50 associated with a healthcare facility and reviewing/selecting shifts. This can also include viewing the caregiver's profile with associated status (as described further below), assignments, etc. This can also include providing directories of other caregivers associated with the healthcare facility and selecting favorites for particular units/teams and/or caregivers. Further, this can include assignment of a caregiver to a particular patient, locating other caregivers within the healthcare facility, and/or communicating with caregivers, as described below.

The mobile caregiver application 300 allows caregivers and staff to use their mobile devices 52 to conduct voice, video, and text messaging between themselves, monitor alerts and calls from assigned patients, and permit voice communications to audio stations 62, 64 mounted in patient rooms adjacent to respective patient beds 54. In some examples, the mobile devices 52 are smartphones, tablet computers, or similar devices. The mobile caregiver application 300 can act as a secondary notification system that supplements a nurse call server 86 of the caregiver communications system 50 that will be described in more detail below.

The calls and alerts from assigned patients and various hospital equipment may originate from the patient beds 54, patient tablets 56, call switches 58, and pillow speaker units 60. Alerts may also originate from smoke alarms 61. In some examples, the audio stations 62, 64 can include a code blue call lever 63 which can be pulled by a caregiver in an emergency such as when a patient is having a medical emergency such as a heart attack. In the example of FIG. 1, the pillow speaker units 60 of the patient beds 54 are coupled to the audio stations 62, 64 by audio station bed connectors (ASBCs) 66. Alternatively, one or more network interface units (NIUs) or wireless interface units (WIUs) can provide the connectivity between the patient beds 54 and respective audio stations 62, 64 instead of the ASBCs 66.

The call switches 58, smoke alarms 61, and audio stations 62, 64 are each communicatively coupled to a respective input/output (I/O) circuit board 68. Each circuit board 68 includes a processor, such as a microprocessor, microcontroller, and the like that receives various alerts and calls, sometimes referred to herein as "alert messages," from the patient beds 54, pillow speaker units 60, smoke alarms 61, and audio stations 62, 64. The processor of each circuit board 68 determines an alert message priority designation for each of the incoming alert messages. For example, alert messages can be designated as normal alert messages or high priority alert messages. Additional types of message priority designations may also be used.

Each circuit board 68 is coupled to a respective dome light 70 which can include multiple lights that are illuminated to indicate a room status. The illumination of the dome light 70 is controlled by the circuit board 68 based on alert conditions occurring in the respective patient room and based on caregiver presence in, or absence from, the patient room. Dome lights 70 are mounted outside each patient room, typically near a doorway to the respective room. In some examples, circuit board 68 are installed in a housing to which the dome lights 70 are mounted. Thus, the circuit board 68 can be located outside the patient rooms adjacent the dome lights 70. Alternatively, the circuit board 68 can be located inside the patient rooms. In either case, the circuit board 68 are considered to be "at" the patient room according to this disclosure.

A locating badge 72 is shown in wireless communication with a remote locator receiver (RLR) 74 which, in turn, is communicatively coupled with the circuit board 68 in the respective patient room in which the RLR 74 is located. The caregiver communications system 50 can include multiple locating badges 72 each worn by a respective caregiver, and multiple RLRs located throughout the healthcare facility. In response to an RLR 74 detecting one or more locating badges 72 in any particular room, a signal or message is communicated to the respective circuit board 68 and the lighting of the dome light 70 is updated accordingly to indicate the presence of a caregiver in the patient room. In certain examples, the locating badges 72 transmit infrared (IR) signals to RLRs 74. Alternative examples are also possible in which radio frequency (RF) transmissions, including ultra-wideband (UWB) transmissions, are made by the locating badges 72 to the RLRs 74 that are in the patent rooms.

Still referring to FIG. 1, each circuit board 68 is communicatively coupled to a Power over Ethernet (PoE) switch 76 which is, in turn, communicatively coupled to a primary staff console 78 (sometimes referred to as a "master nurse station"), a secondary staff console 80, and a staff terminal 82. PoE switch 76 is communicatively coupled to a voice over Internet protocol (VoIP) Switch and Enterprise server 84 which is, in turn, coupled to a nurse call server 86 via Ethernet infrastructure, illustrated diagrammatically as network 90 in FIG. 1. Also, the mobile devices 52 are communicatively coupled to the VoIP Switch and Enterprise server 84, which can provide access on the mobile devices 52 to an electronic medical records (EMR) server 94, an admission, discharge, transfer (ADT) server 96, and additional servers 98 via the network 90.

The call switches 58, pillow speaker units 60, audio stations 62, 64, ASBC's 66, circuit board 68, dome light 70, PoE switch 76, primary staff console 78, secondary staff console 80, staff terminal 82, VoIP Switch and Enterprise server 84, and nurse call server 86 are illustrative of a diagrammatic nurse call system portion of the caregiver communications system 50 and that nurse call system architecture will vary from one healthcare facility to the next.

The patient tablets 56 can also be included as part of the nurse call system portion of the caregiver communications system 50. The patient tablets 56 are used by patients to send requests such as requests for pain medication, requests for bathroom assistance, food requests, drink requests, ice chips requests, requests for assistance with personal care, and the like. In the illustrative example, the patient tablets 56 communicate wirelessly with wireless access points (WAP) 88 which, in turn, communicate with a patient tablet communications server 92. The patient tablet communications server 92 communicates the patient requests, which are also considered to be alert messages, to the nurse call server 86 via a network 90.

The alert messages originating from the patient beds 54 can include alert messages relating to a bed exit of the patient from a patient bed 54, patient position on a patient bed 54 exceeding a threshold, patient movement on a patient bed 54 exceeding a threshold or falling below a threshold, siderail position (e.g., siderail down) of a patient bed 54, casters of a patient bed 54 not being braked, angle of a head section of a patient bed 54 being below a threshold angle (e.g., 30 degrees), an upper frame of a patient bed 54 not being in its lowest position relative to a base frame of the patient bed 54, a bed component of a patient bed 54 exceeding a threshold temperature, a mattress bladder of a patient bed 54 falling below a threshold pressure, a pneumatic system error or failure of a patient bed 54, an actuator error or failure of a patient bed 54, an overcurrent condition of a component of a patient bed 54, a power system error or failure of a patient bed 54, and power disconnection from a patient bed 54.

Still referring to FIG. 1, the caregiver communications system 50 includes the electronic medical records (EMR) server 94 and the admission, discharge, transfer (ADT) server 96. The caregiver communications system 50 may also include additional servers 98. The nurse call server 86, EMR server 94, ADT server 96, and additional servers 98 are accessible on the mobile devices 52 via the VoIP Switch and Enterprise server 84 and network 90.

In certain examples, the additional servers 98 can include, for example, a real time locating system (RTLS) server that is communicatively coupled to RLRs 74. In such examples, the locating badges 72, RLRs 74, and RTLS server form a real time locating system portion of the caregiver communications system 50. Staff locating information can be communicated from the RTLS server to the nurse call server 86 via the network 90.

In some examples, the additional servers 98 can include a server that manages the routing of alert messages and related staff information to the mobile device 52. In general, alert messages relating to particular patients or particular rooms assigned to particular caregivers are sent to the mobile device 52 of that particular caregiver. The alert messages may originate from the patient beds 54, pillow speaker units 60, and patient tablets 56. Additionally, it is also possible that alert messages originating from other types of equipment may be communicated to the mobile devices 52 of assigned caregivers as well.

The features and functions of the mobile caregiver application 300 are described below in more detail that show various screen shots that can appear on the mobile devices 52. By seeing the functionality represented in each of the screen shots and by considering the following description, those skilled in the art will be enabled to make and use the mobile caregiver application, and its variant embodiments, contemplated herein. It should be appreciated that the screen shots of this disclosure are exemplary in nature and are provided to give a general sense of the type of information that may appear on a display screen of any given mobile device 52 during use of the mobile caregiver application by the caregivers and staff. Thus, the screen shots are merely individual examples from a practically unlimited number of possibilities. That is, the information such as alert messages, staff names, staff locations, room name formats, unit names, and the like may vary from healthcare facility to healthcare facility and, in fact, varies in any given healthcare facility throughout any given day in response to the various incoming alert messages, for example.

Figure 2:
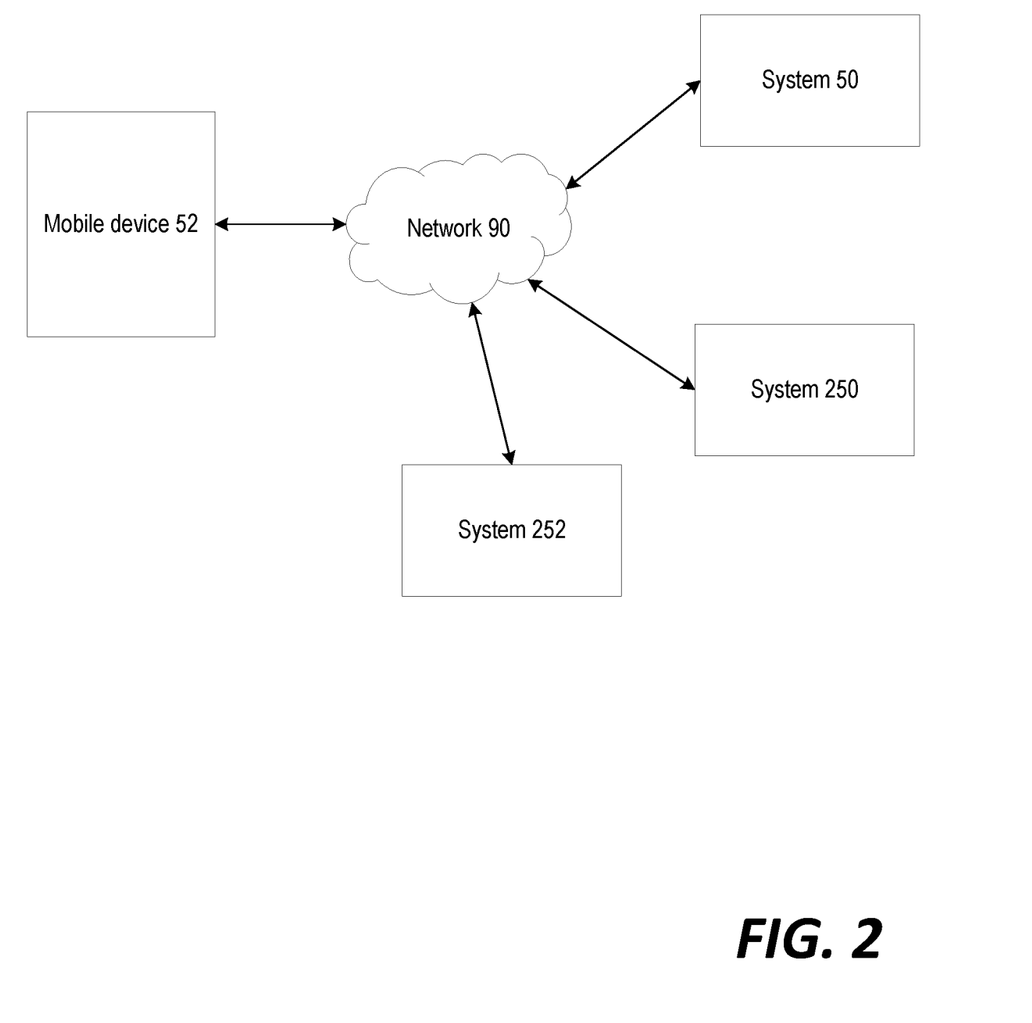
FIG. 2 schematically illustrates the mobile caregiver application connected to the caregiver communication systems of multiple healthcare facilities.

FIG. 2 illustrates one of the mobile devices 52 used by caregivers and staff. In this example, the mobile device 52 is connected via the network 90 to the caregiver communications system 50, which is a first caregiver site with which the caregiver or staff is associated, such as a healthcare facility like a hospital, clinic, and the like. The mobile device 52 is also connected via the network 90 to one or more additional sites with which the caregiver or staff is associated such as caregiver communications systems 250, 252. The caregiver communications systems 250, 252 are associated with other healthcare facilities, such as other hospitals and clinics, and can be configured in a manner similar to that of the caregiver communications system 50.

For instance, in this example, a caregiver can use her mobile device 52 to communicate through the caregiver communications system 50 while the caregiver is connected to the first healthcare facility associated with the caregiver communications system 50. With the mobile device 52 connected to the caregiver communications system 50, the caregiver can receive communications (e.g., notifications relating to alerts, messages, and/or other items) associated with the care of the patients in the first healthcare facility, as described above. Additional details regarding the types of notifications that can be sent are provided in U.S. Patent Application No. 63/109,464, titled MANAGING CAREGIVER MESSAGES, and filed on Nov. 4, 2020, the entirety of which is hereby incorporated by reference.

Continuing with this example, assume that the caregiver also provides care for patients located at other healthcare facilities. If these other healthcare facilities are unaffiliated or otherwise not electronically connected to the first healthcare facility associated with the caregiver communications system 50, the communications associated with these other healthcare facilities are provided on wholly-separate systems, such as the caregiver communications systems 250, 252. This means that the caregiver will not receive notifications from the caregiver communications systems 250, 252 while the mobile device 52 is connected to the caregiver communications system 50. Further, other caregivers and staff connected to the caregiver communications systems 250, 252 cannot communicate nor know the status of the caregiver when she is disconnected from the caregiver communications systems 250, 252.

As described further below, the mobile caregiver application 300 on the mobile device 52 allows the caregiver to be logged into communication systems for multiple healthcare facilities at the same time, such as the caregiver communications systems 50, 250, 252. In this manner, the mobile device 52 can receive notifications associated with two or more of the caregiver communications systems 50, 250, 252 such that the caregiver can monitor patients at different healthcare facility locations at the same time.

The network 90 can include any type of wired or wireless connections or any combinations thereof. Examples of wired connections include fiber optic, ethernet, and other wired computer networking technologies. Examples of wireless connections include broadband cellular networks such as 4G and 5G, Wi-Fi, Bluetooth, and the like.

Figure 3:
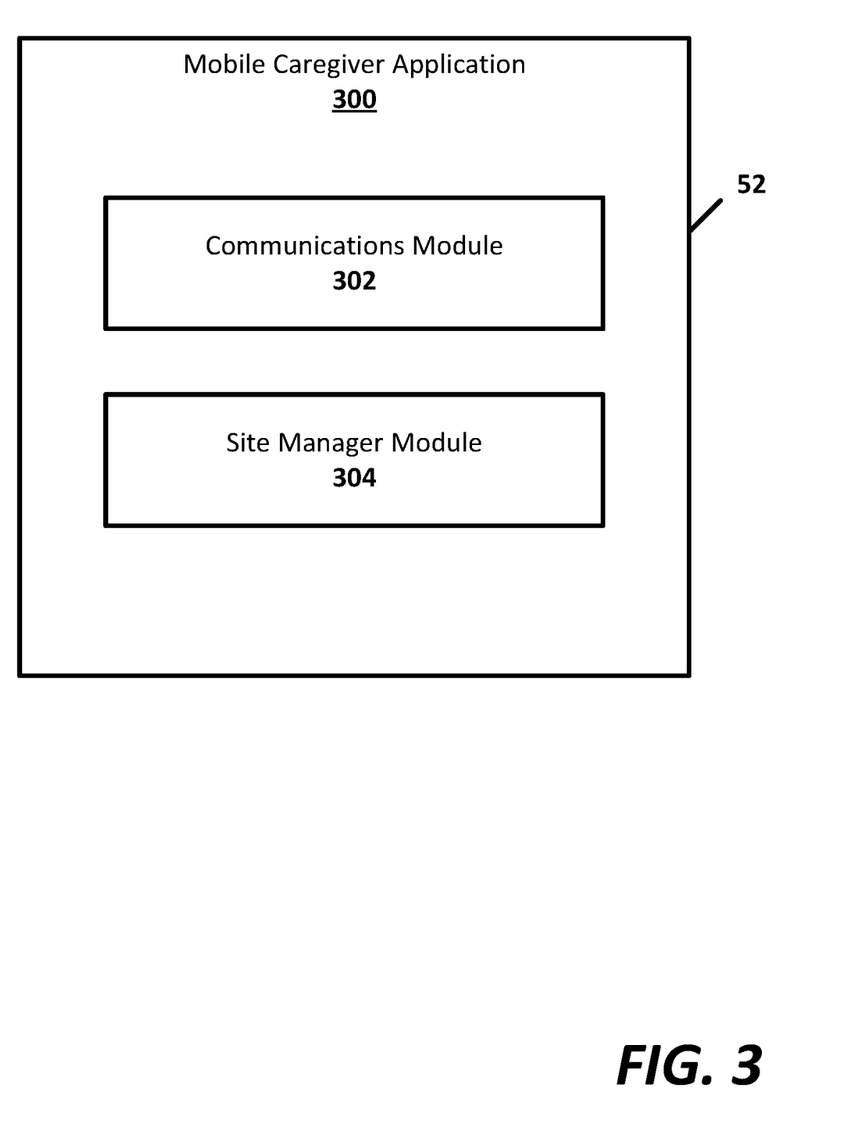
FIG. 3 schematically illustrates the mobile caregiver application of FIG. 2.

FIG. 3 schematically illustrates the mobile caregiver application 300 on the mobile device 52. In further embodiments, the mobile caregiver application 300 can also be operated on one or more servers connected to the network 90 such as, for example, the nurse call server 86, EMR server 94, ADT server 96, and additional servers 98.

The mobile caregiver application 300 is available for downloading on the mobile device 52 from an application store 99 (see FIG. 1) accessible via the Internet, such as on iOS and Android operating systems. Alternatively, the mobile caregiver application 300 can also be downloaded on the mobile devices 52 by connecting the mobile device to a data storage device that has the mobile caregiver application 300 stored thereon. In some examples, the mobile caregiver application 300 is downloaded onto the mobile devices 52 under the supervision and authorization of an administrator.

As shown in the example depicted in FIG. 3, the mobile caregiver application 300 includes a communications module 302 and a site manager module 304. In this example, the mobile caregiver application 300 is the Voalte Me caregiver application from Hillrom of Batesville, Ind., although other configurations are possible. The mobile caregiver application 300 may include fewer or additional software modules as desirable such that the software modules described herein are provided for illustrative purposes only.

The communications module 302 generally facilitates communications between the mobile caregiver application 300 and one or more sites, such as the caregiver communications systems 50, 250, 252. See generally FIGS. 4 and 8-9. In this example, the communications module 302 provides communications with three types of site: active, passive, and dormant.

Figure 4:
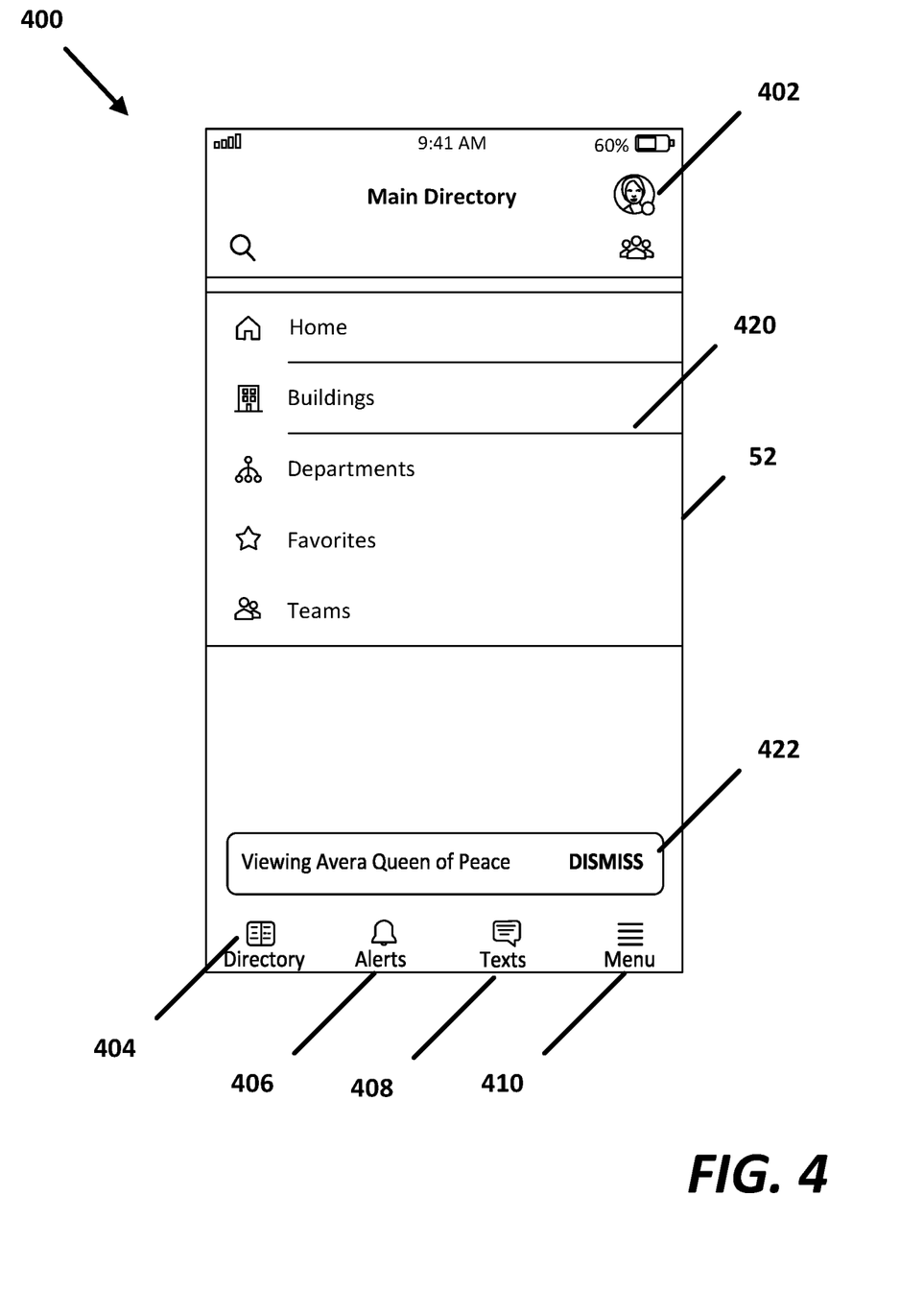
FIG. 4 illustrates a user interface of the mobile caregiver application of FIG. 3 allowing access to various resources associated with a healthcare facility.

An active site is the current communications system to which the mobile caregiver application 300 is connected. As depicted in FIG. 4 described below, the caregiver or staff can actively engage with the active site using the mobile device 52. A passive site is a communications system that the caregiver or staff is logged into and can receive notifications, but is not the current, active site on the mobile device 52 to which the mobile caregiver application 300 is connected. A dormant site is a communications system that is listed on the list of accessible sites (see FIG. 6) on the mobile device 52, but to which the mobile caregiver application 300 is not currently logged into nor connected.

In this example, an active site is associated with the caregiver communications system 50, a passive site is associated with the caregiver communications system 250, and a dormant site is associated with the caregiver communications system 252. In other examples, there can be multiple passive and dormant sites.

In these examples, each of the sites that is managed by the communications module 302 is a server or other computing device associated with one of the caregiver communications systems 50, 250, 252. In this example, one or more of the sites is a Voalte server provided by Hillrom of Batesville, Ind., although other configurations are possible.

Referring now to FIG. 4, an example user interface 400 generated by the communications module 302 on the mobile device 52 is shown. This user interface 400 generally provides information and communication between the mobile device 52 and the active site on the mobile device 52, such as the caregiver communications system 50.

The user interface 400 includes a profile item 402 that depicts information, such as a picture or initials, of the caregiver that is currently using the mobile device 52. Selection of the profile item 402 can provide additional details about the caregiver, such as name, telephone number, role, etc.

The user interface 400 also includes buttons 404, 406, 408, and 410 that allow the caregiver to select various information associated with the active site. Button 404 allows the caregiver to select a directory of people associated with the caregiver communications system 50. As depicted, a portion 420 of the user interface 400 can filter the listed people based upon various criteria, such as buildings, departments, favorites (as selected by the caregiver), and/or teams.

The buttons 406 and 408 allow the caregiver to access alerts and texts received from the active site. See FIGS. 8-9 described below. The button 410 allows the user to access settings associated with the mobile caregiver application 300, such as those shown in FIG. 5 described below.

The user interface 400 also includes a notification 422 that reminds the caregiver of the active site ("Avera Queen of Peace" hospital) on the mobile caregiver application 300. This notification can take various forms, such as a toast or snackbar that provides the active site information.

In this embodiment, the notification 422 is provided when the mobile caregiver application 300 is launched (after a forced quit) on the mobile device 52 and/or when the mobile caregiver application 300 is brought to the foreground (i.e., accessed) on the mobile device 52. As depicted in the example, the notification 422 can be dismissed by the caregiver as desired.

The site manager module 304 of FIG. 3 manages the active, passive, and dormant sites that have been configured on the mobile device 52. The site manager module 304 allows the caregiver to switch between the sites and log into and out of the sites. The site manager module 304 also allows the caregiver to add new sites and remove existing sites from the mobile caregiver application 300.

Figure 5:
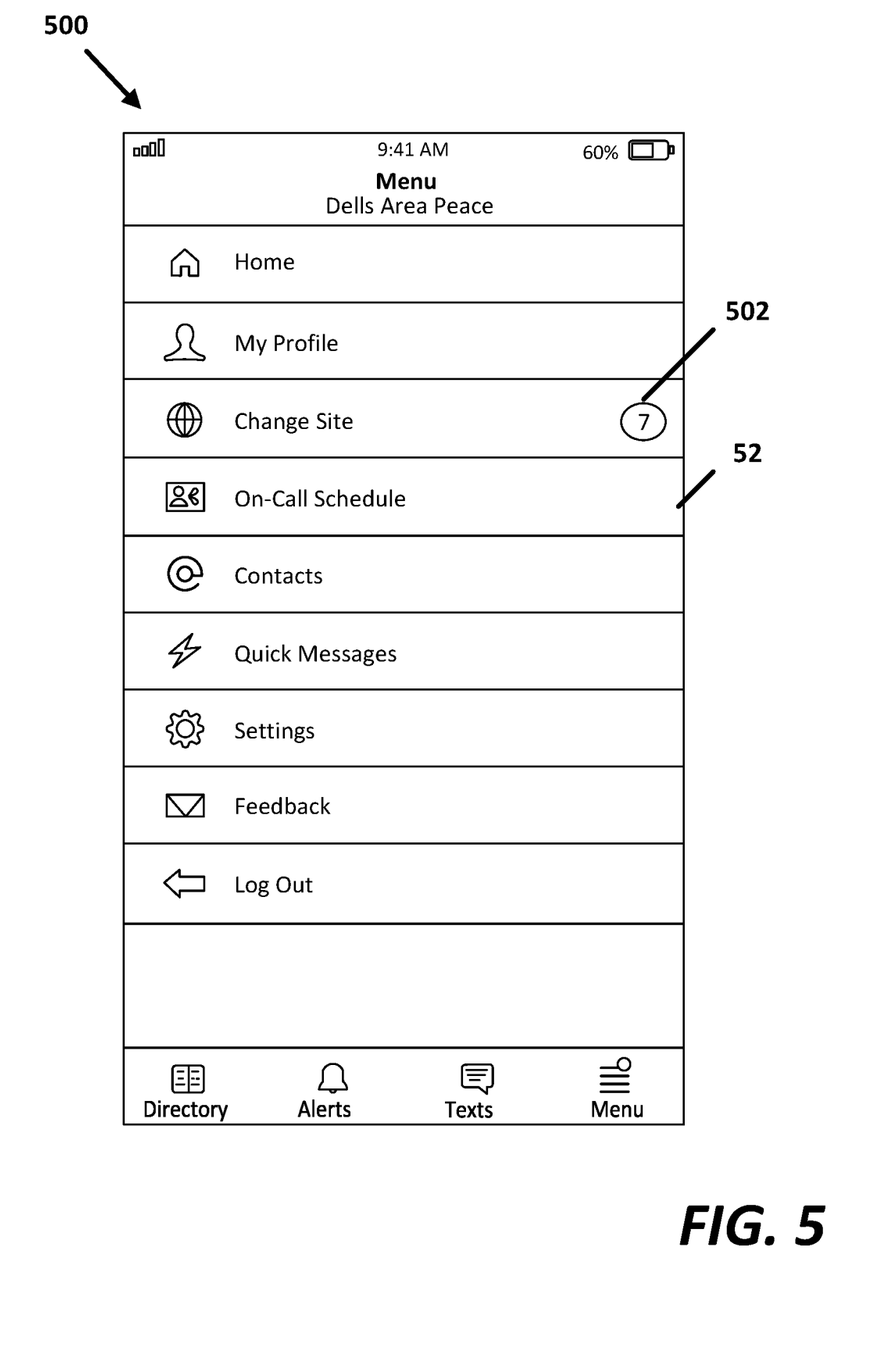
FIG. 5 illustrates another user interface of the mobile caregiver application of FIG. 3 providing settings for the mobile caregiver application.

Referring now to FIGS. 5-8, when the caregiver selects the button 410 on the user interface 400, an example user interface 500 is shown as in FIG. 5, which provides the user with various settings associated with the mobile caregiver application 300. One of these settings on the user interface 500 is a change site item 502.

Figure 6:
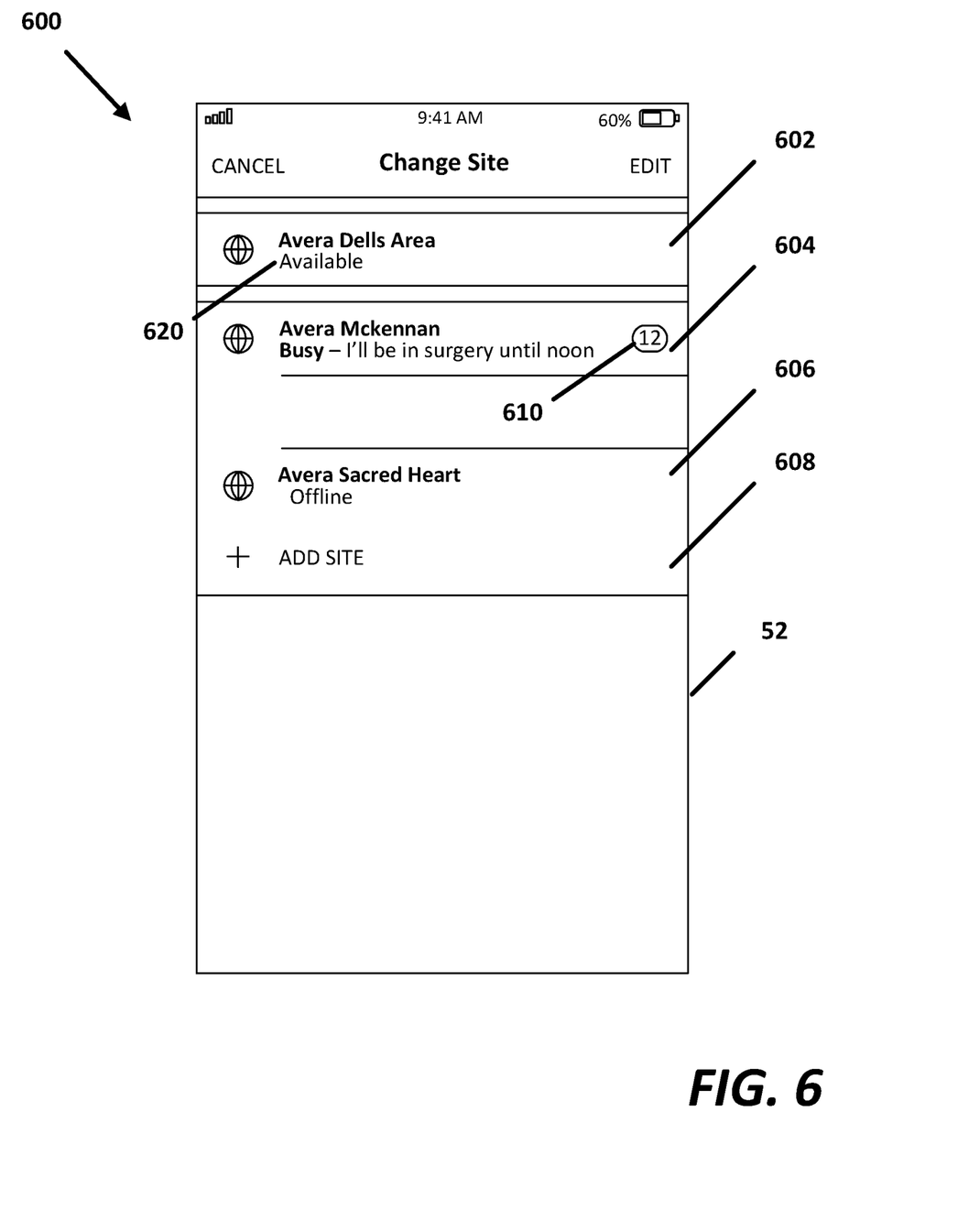
FIG. 6 illustrates another user interface of the mobile caregiver application of FIG. 3 providing a list of active, passive, and dormant sites that are configured within the mobile caregiver application.

Upon receiving selection of the change site item 502 on the user interface 500, the mobile caregiver application 300 displays a user interface 600 shown in FIG. 6. The user interface 600 lists every site that has been configured on the mobile caregiver application 300. The user interface 600 generally allows the caregiver to switch between sites and to define a status for each site.

More specifically, the user interface 600 shows all of the sites 602, 604, 606 that have been configured for the mobile caregiver application 300. The site 602 that is active is listed at the top of the user interface 600. The site 604 that is passive is listed below the active site. The site 606 that is dormant is listed below the passive site. When multiple passive or dormant sites are listed, the sites can be listed in an order, such as chronological from most recent to least recent, alphanumeric based upon site name, etc.

The caregiver can select the site 604, which is a passive site, to switch from the site 602 to the site 604. Upon receiving selection of the site 604, the mobile caregiver application 300 will display the user interface 400 showing items relevant to the site 604. The site 602 will thereupon switch from the active site to a passive site. Advantageously, this allows the caregiver to access and view the notifications and/or messages from the site 604, while continuing to remain connected to the site 602 and to receive notifications from the site 602.

In another illustrative example, the caregiver can select the site 606, which is a dormant site, to switch from the site 602 to the site 606. Upon receiving selection of the site 606, the mobile caregiver application 300 will request that the user log into the site 606 by providing credentials (e.g., username and password). These credentials can be cached and automatically provided in some instances. The switch is then initiated using stored reconnection information (e.g., location, credentials, configuration, etc.) for the site 606.

Upon receiving the necessary credentials, the mobile caregiver application 300 will display the user interface 400 showing items relevant to the site 606. The site 602 will thereupon switch from the active site to a passive site. Advantageously, this can provide a technical effect by allowing the caregiver to access and view the notifications and/or messages from the site 606 when switched from dormant to active, while continuing to remain connected to the sites 602, 604, and thereby continuing to receive notifications from the sites 602, 604.

Once the user switches to another site (either passive or dormant), the notification 422 (see example shown in FIG. 4) is provided to remind the caregiver of the active site on the mobile caregiver application 300. The previous active site switches to a passive site. In case of errors connecting to the selected site, the caregiver can cancel the existing switch attempt and see the list of available sites on the user interface 600.

The mobile caregiver application 300 maintains a session with the active site and all passive sites so that messages from the active and passive sites can be provided to the caregiver at the mobile device 52. This therefore allows the caregiver to monitor multiple sites at different hospitals or clinics on a single mobile device and easily switch between the sites.

In addition to providing the list of available sites, a badge counter 610 is provided for any of the sites which have unread notifications. In this example, the site 604 has "12" notifications for the caregiver. The caregiver can access these notifications by selecting the site 604 to make the site 604 active and access the notifications on the user interface 400. In some examples, an aggregate of all notifications (e.g., from all passive sites) can also be provided.

Each of the sites 602, 604, 606 on the user interface 600 also provides a status 620 for the caregiver. In this example, the status 620 can be set to "Available", "Busy", or "Unavailable". This allows other caregivers associated with each of the sites 602, 604, 606 to see the status of the caregiver on the mobile device 52. The status "Available" signifies that the caregiver is free to read messages and respond. The status "Busy" signifies that the caregiver is currently unable to read or respond to messages but may become available after a specific event (e.g., surgery, phone call, etc.). The status "Unavailable" signifies that the caregiver is currently unable to read or respond to messages for an undetermined amount of time.

For instance, another caregiver logged into the site 602 can see that the caregiver is "Available", while another caregiver logged into the site 604 can see that the caregiver is "Busy". Thus, a first status at the site 602 is different from a second status at the site 604.

In this example, the status can be set automatically or manually by the caregiver. For instance, the status can be automatically set to "Available" when the caregiver logs into a site. The status can be automatically set to "Busy" when the caregiver receives a call on the mobile device 52 or has a calendar appointment.

Figure 7:
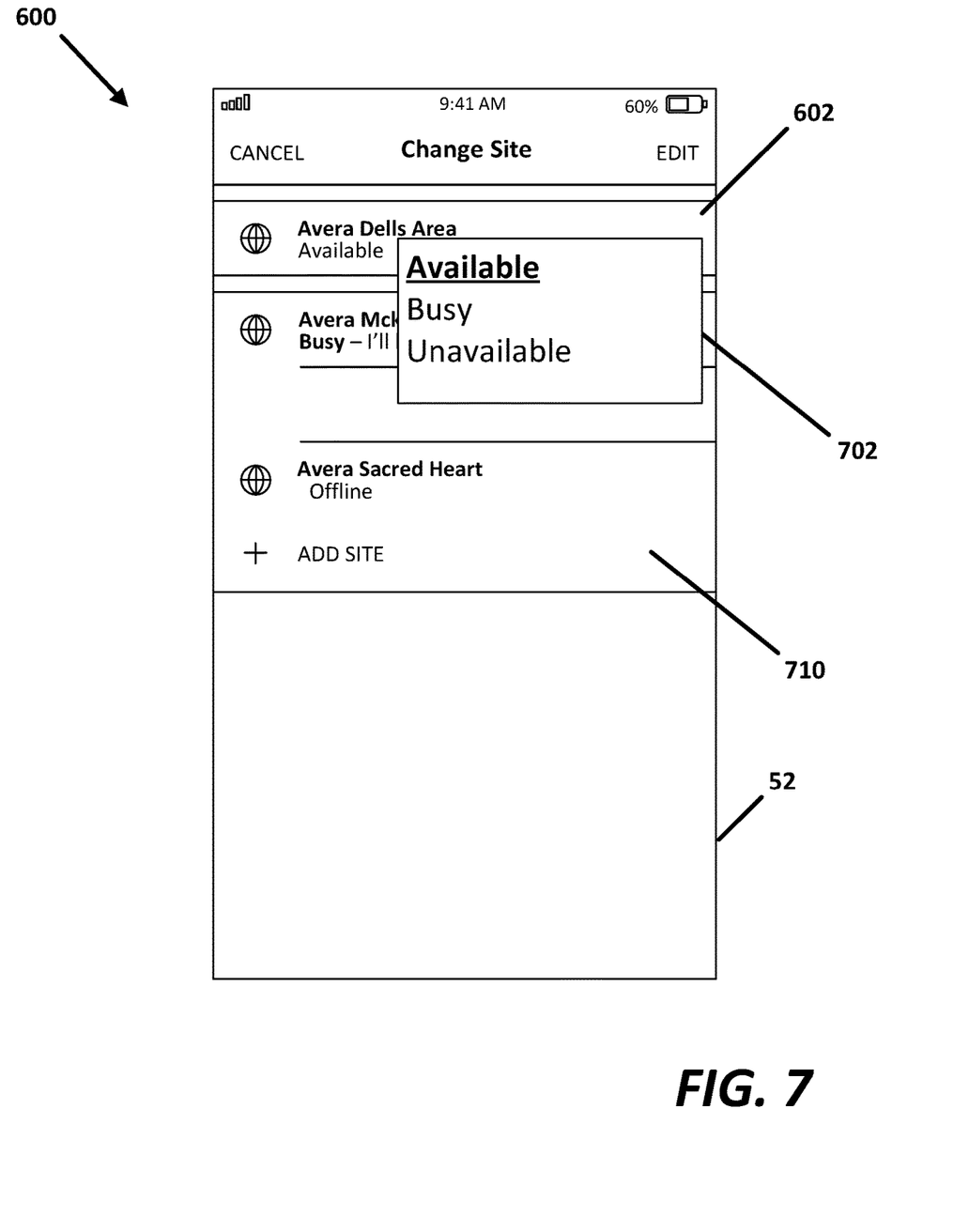
FIG. 7 illustrates the user interface of FIG. 6 with controls for setting a status of the caregiver on the communications system of one of the healthcare facilities.

As shown in FIG. 7, the caregiver can manually set the status 620 by selecting the status 620. A menu 702 is provided that allows the caregiver to select among the statuses. Further, the caregiver can customize a status. For instance, a status for the site 604 has been customized by the caregiver to indicate she will be in surgery until noon.

Referring back to FIG. 6, the status for the site 606 defaults to "Offline" because the site 606 is dormant. Many other configurations are possible.

Figure 8:
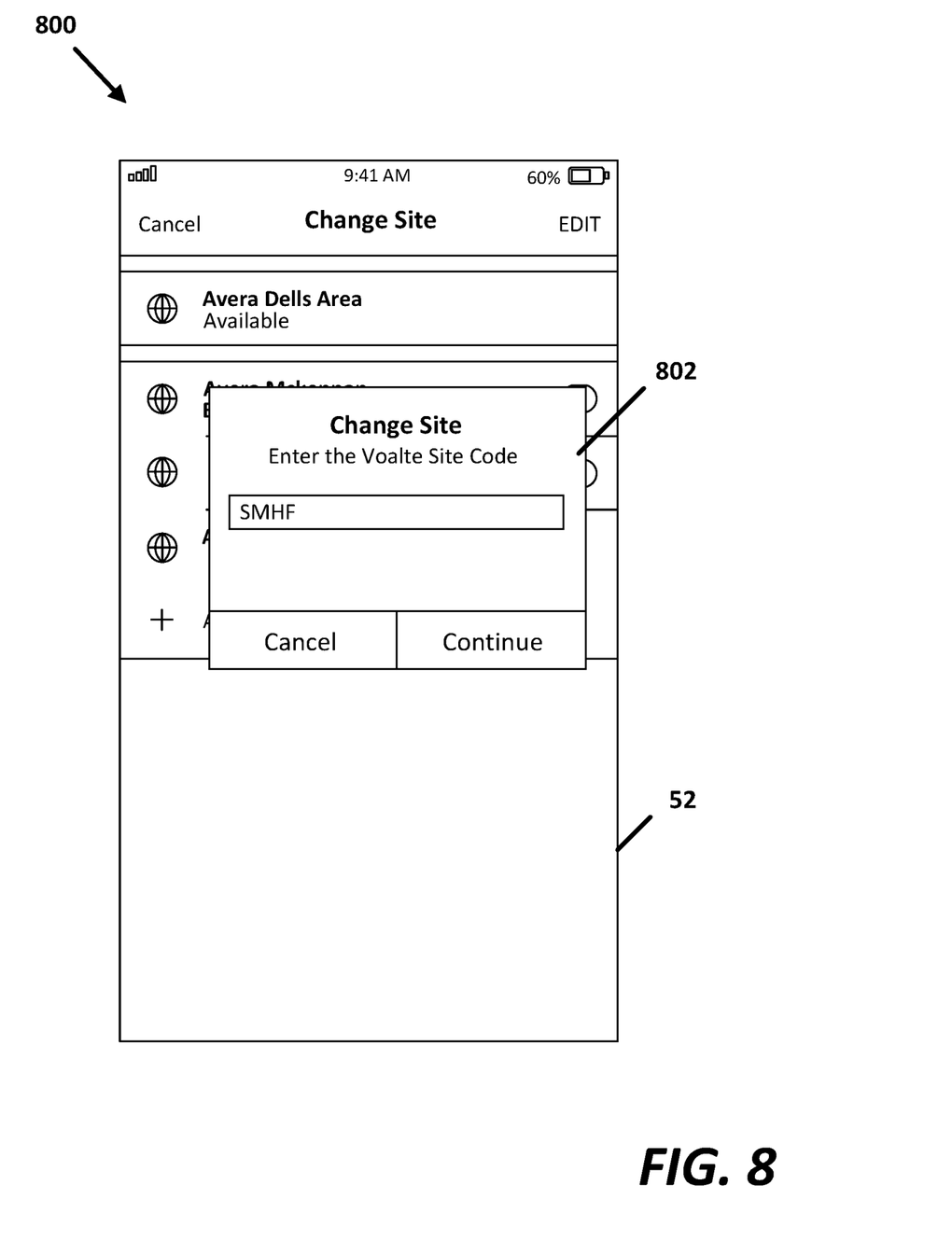
FIG. 8 illustrates another user interface of the mobile caregiver application of FIG. 3 allowing input of another healthcare facility to be configured with the mobile caregiver application.

The caregiver can add and remove sites on the user interface 600. For instance, upon receiving selection of an add site item 710, the mobile caregiver application 300 display a user interface 800 as shown in FIG. 8 that allows for a new site to be added.

Specifically, an input box 802 is provided to allow the user to identify the site to be added. There are various ways the site can be identified. For instance, the caregiver can provide a site name, if known. As the input is provided by the caregiver, the input box 802 can attempt to autocomplete the site name based upon a list of available sites.

The caregiver can also give other information associated with a site, such as a site code. A site code can be a unique identifier (GUID) that identifies a site. For instance, the site code can be an alphanumeric code that is provided to the caregiver. The caregiver can input this code into the input box 802 to connect the mobile caregiver application 300 to the new site. If the site code is invalid, the caregiver is shown an error message and allowed to re-enter the site code. Similarly, if the site code already exists in the sites that are configured with the mobile caregiver application 300 (see user interface 600), an error is displayed indicating that the site is already configured, and the caregiver is allowed to enter another site.

In another example, the caregiver can optionally provide connection details for the site, such as a uniform resource locator or IP address associated with the site. Upon receiving identification information for the site, the mobile caregiver application 300 is programmed to automatically configure the site (e.g., by converting a site name into an IP address using a domain name system). For instance, the mobile caregiver application 300 can communicate with a server that manages configuration information for a plurality of sites and/or communicate with the specified site to receive connection and credential information. This process can happen automatically or manually depending on how the mobile caregiver application 300 is configured.

For instance, in one example, the mobile caregiver application 300 maintains a cache of the information necessary to connect to and communicate with each of the active, passive, and dormant sites configured for the mobile caregiver application 300. In this example, the cached information can include the following.

| Site code | Site name | Connection type | Address | Credentials |
|---|---|---|---|---|
| 12345 | Avera Dells Area | https | www.averadells.org/siteA | username/pass (encrypted) |
| 13456 | Avera Mckennan | IP | 128.16.254.1 | SSO |
| 14567 | Avera Sacred Heart | https | www.averasacred.org/siteB | username/pass (encrypted) |

Once a new site is added successfully, the site is entered on the user interface 600 as a dormant site. Upon selection of the new site, the caregiver is prompted to provide credentials to allow the mobile caregiver application 300 to access the new site. In some examples, the caregiver can access the new site using a single sign-on process.

Figure 9:
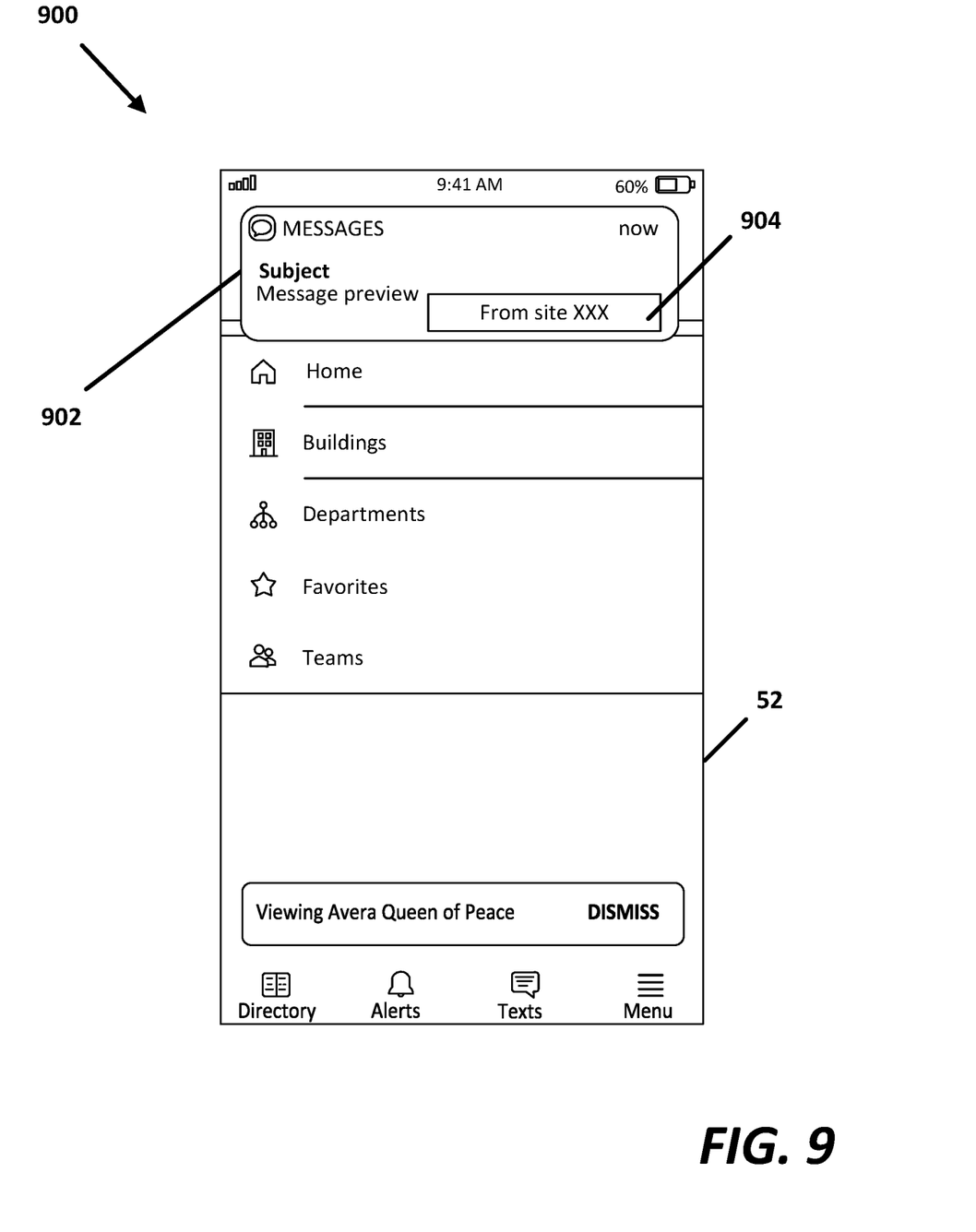
FIG. 9 illustrates another user interface including a notification from one of the healthcare facilities configured with the mobile caregiver application.
Figure 10:
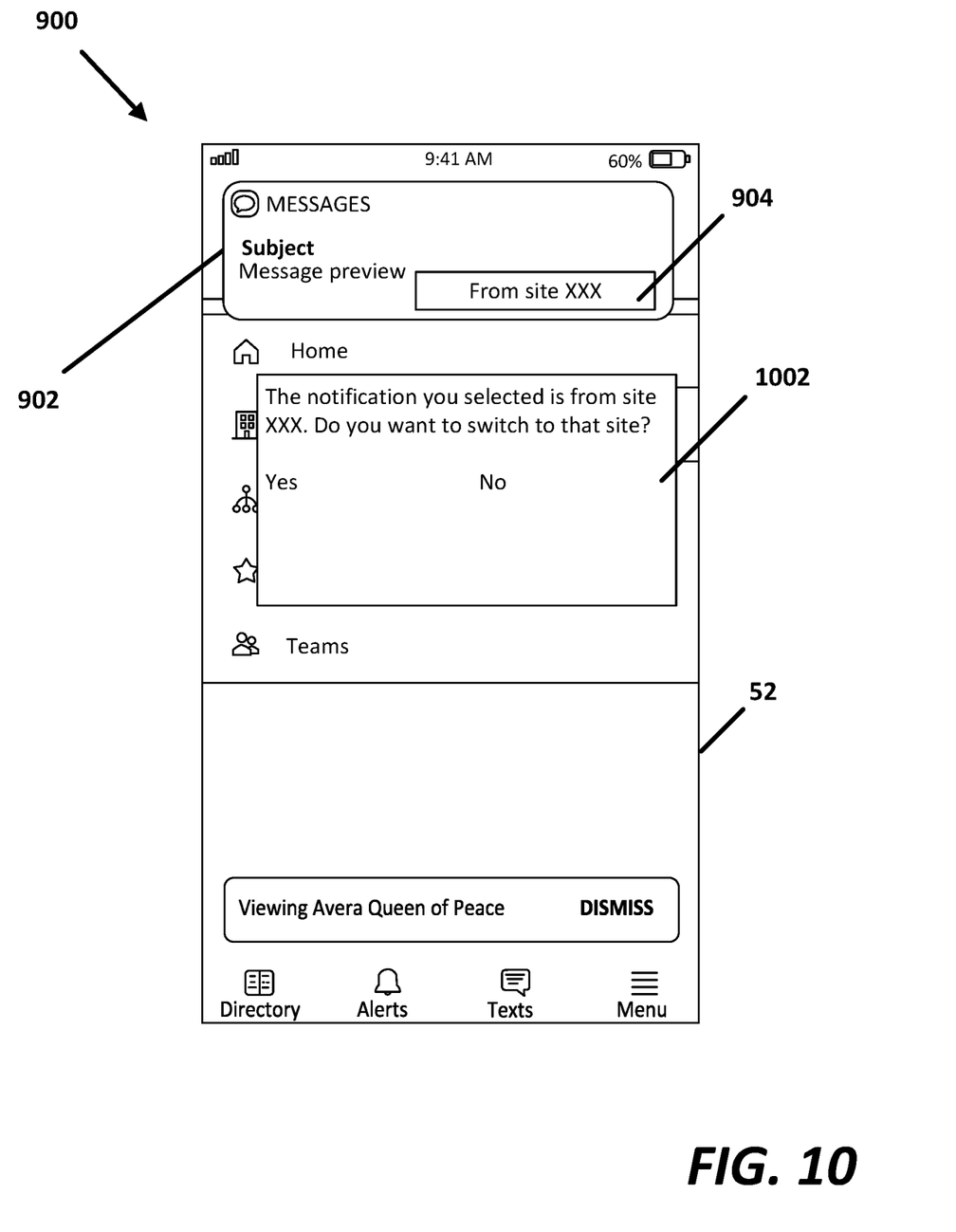
FIG. 10 illustrates the user interface of FIG. 9 with a warning control for switching to another healthcare facility associated with the notification on the mobile caregiver application.

Referring now to FIGS. 9-10, an example user interface 900 is shown. This interface can be generated by the mobile caregiver application 300 or another application running on the mobile device 52. An example notification 902 is shown from one of the sites (active or passive) into which the mobile caregiver application 300 is connected. Aspects associated with the notification (e.g., notification type, sound, etc.) can be configured by the caregiver.

In this example, the notification 902 includes a subject and preview of contents for the notification. For instance, if the notification 902 is associated with a message sent by another caregiver, the notification 902 can include information such as the other caregiver's name, a subject for the message, and at least a portion of the message contents. Similarly, if the notification 902 is associated with an alert for a patient, the notification can include the patient's name, an identification for the alert, and details associated with the alert.

Notifications from active and passive sites also provide an indicator 904 identifying the origin of the notification 902. In this example, the indicator 904 states that the notification is from site XXX such as, for example, the name of the hospital associated with the site, site code, or other identifying information, including a custom name provided by the caregiver for the site.

The caregiver can select the notification 902 to access the message associated with the notification. If the notification 902 is from a passive site, a warning box 1002 is provided as depicted in FIG. 10. This warning box 1002 states that the mobile caregiver application 300 will switch the passive site associated with the notification to active to access the message if the caregiver wishes to proceed. The warning can be turned off by the caregiver, if desired.

If the caregiver proceeds to the passive site to access the contents of the message, the passive site is moved to the active site, and the prior active site is moved to a passive site on the user interface 600. The caregiver is provided with the contents of the message by the mobile caregiver application 300. The caregiver can also be provided with a notification (e.g., snackbar) that allows the caregiver to switch the mobile caregiver application 300 back to the previous active site after reviewing the message, if desired.

The example computing devices described herein can each include at least one central processing unit ("CPU"), a system memory, and a system bus that couples the system memory to the CPU. The system memory includes a random access memory ("RAM") and a read-only memory ("ROM"). A basic input/output system that contains the basic routines to transfer information between elements within the computing device, such as during startup, is stored in the ROM. The computing device further includes a mass storage device. The mass storage device can store software instructions and data such as therapy protocols and lookup tables.

The mass storage device is connected to the CPU through a mass storage controller connected to the system bus. The mass storage device and its associated computer-readable storage media provide non-volatile, non-transitory data storage for the computing device. Although the description of computer-readable storage media contained herein refers to a mass storage device, such as a hard disk or solid state disk, it should be appreciated by those skilled in the art that computer-readable data storage media can include any available tangible, physical device or article of manufacture from which the CPU can read data and/or instructions. In certain embodiments, the computer-readable storage media comprises entirely non-transitory media.

Computer-readable storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the computing device.

According to various embodiments, the computing device can operate in a networked environment using logical connections to other devices connected to the network 90, including a wireless network, the Internet, or any other type of network. The computing device may connect to the network 90 through a network interface unit connected to the system bus. The network interface unit may also be utilized to connect to other types of networks and remote computing systems. The computing device also includes an input/output controller for receiving and processing input from a number of other devices, including a touch user interface display screen, or another type of input device. Similarly, the input/output controller may provide output to a touch user interface display screen or other type of output device.

As mentioned briefly above, the mass storage device and the RAM of the computing device can store software instructions and data. The software instructions include an operating system suitable for controlling the operation of the computing device. The mass storage device and/or the RAM also store software instructions, that when executed by the CPU, cause the computing device to provide the functionality discussed in this document.

The various embodiments described above are provided by way of illustration only and should not be construed to be limiting in any way. Various modifications can be made to the embodiments described above without departing from the true spirit and scope of the disclosure.

What is claimed is:

1. An electronic device for managing notifications for a caregiver associated with multiple healthcare facilities, the electronic device comprising:
   a processor; and
   a memory encoding instructions which, when executed by the processor, cause the processor to:
      connect to an active site belonging to a first communications system server connected to the electronic device;
      connect to a passive site belonging to a second communications system server connected to the electronic device, the second communications system server being different from the first communications system server;
      generate a user interface providing information associated with the active site;
      receive the notifications from both the active site and the passive site;
      switch the active site to passive and the passive site to active upon receipt of an input on the user interface from the caregiver to access the notifications from the passive site, and provide access on the user interface to notifications from the second communications system server while continuing to remain connected to the first communications system server;
      after access of the notifications from the second communications system server, present a switching notification, and when a response to the switching notification is received on the user interface, switch a previous active site back to active and a previous passive site back to passive;
      provide a first status for the electronic device at the first communications system server and a second status for the electronic device at the second communications system server, wherein the first status is different from the second status; and
      maintain a cache of information to connect to each of the active site and the passive site, wherein the cache of information for each of the active site and the passive site includes a site name, a connection type, an address, and credential information.

2. The electronic device of claim 1, further comprising instructions which, when executed by the processor, cause the processor to maintain a session with the active site and a plurality of passive sites such that messages from the active site and the plurality of passive sites are provided to the caregiver at the electronic device.

3. The electronic device of claim 2, further comprising instructions which, when executed by the processor, cause the processor to provide a badge counter for any one of the plurality of passive sites which have unread notifications.

4. The electronic device of claim 3, further comprising instructions which, when executed by the processor, cause the processor to provide access to the unread notifications in response to receiving a selection of one of the plurality of passive sites to switch the selected one of the plurality of passive sites to active.

5. The electronic device of claim 1, further comprising instructions which, when executed by the processor, cause the processor to provide customization of the first status and the second status.

6. The electronic device of claim 1, further comprising instructions which, when executed by the processor, cause the processor to automatically set the first status and the second status.

7. The electronic device of claim 1, wherein the notifications are received from multiple passive sites connected to the electronic device.

8. The electronic device of claim 1, further comprising instructions which, when executed by the processor, cause the processor to receive a selection of the passive site to switch the passive site to active and to switch the active site to passive.

9. The electronic device of claim 1, further comprising instructions which, when executed by the processor, cause the processor to receive a selection of a notification to access a message associated with the notification, and when the notification is from the passive site, display a warning box to indicate that the passive site associated with the notification will switch to active.

10. The electronic device of claim 1, further comprising instructions which, when executed by the processor, cause the processor to add another site upon receipt of a site code.

11. The electronic device of claim 1, wherein the address includes an internet protocol (IP) address or a hypertext transfer protocol secure (HTTPS) address.

12. A non-transitory computer readable storage media including computer readable instructions which, when read and executed by a computing device, cause the computing device to:
connect to an active site belonging to a first communications system server connected to an electronic device;
connect to a passive site belonging to a second communications system server connected to the electronic device, the second communications system server being different from the first communications system server;
generate a user interface providing information associated with the active site;
receive notifications from both the active site and the passive site;
switch the active site to passive and the passive site to active upon receipt of an input on the user interface from a caregiver to access the notifications from the passive site, and provide access on the user interface to notifications from the second communications system server while continuing to remain connected to the first communications system server;
after access of the notifications from the second communications system server, present a switching notification, and when a response to the switching notification is received on the user interface, switch a previous active site back to active and a previous passive site back to passive;
receive a first status for the electronic device at the first communication system server and a second status for the electronic device at the second communication system server, and wherein the first status is different from the second status; and
maintain a cache of information to connect to each of the active site and the passive site, wherein the cache of information for each of the active site and the passive site includes a site name, a connection type, an address, and credential information.

13. The non-transitory computer readable storage media of claim 12, further including computer readable instructions which, when read and executed by the computing device, cause the computing device to:
receive a selection of the passive site to switch the passive site to active and to switch the active site to passive.

14. An electronic device for managing notifications for a caregiver associated with multiple healthcare facilities, the electronic device comprising:
a processor; and
a memory encoding instructions which, when executed by the processor, cause the processor to:
connect to a first site belonging to a first communications system server connected to the electronic device;
generate a user interface;
display first contact information on the user interface for first caregiver team members associated with the first site;
communicate a first message to at least one of the first caregiver team members;
connect to a second site belonging to a second communications system server connected to the electronic device, the second communications system server being different from the first communications system server;
display second contact information on the user interface for second caregiver team members associated with the second site;
communicate a second message to at least one of the second caregiver team members;
receive notifications from both the first site and the second site;
switch the first site from active to passive and the second site from passive to active upon receipt of an input on the user interface to access the notifications from the second site, and provide access on the user interface to notifications from the second communications system server while continuing to remain connected to the first communications system server when the first site is switched from active to passive; and
after access of the notifications from the second site, present a switching notification, and when a response to the switching notification is received on the user interface, switch the first site back to active and the second site back to passive;
receive a first status for the electronic device at the first communication system server and a second status for the electronic device at the second communication system server, wherein the first status is different from the second status; and
maintain a cache of information to connect to each of the active site and the passive site, wherein the cache of information for each of the active site and the passive site includes a site name, a connection type, an address, and credential information.

15. The electronic device of claim 14, further comprising instructions which, when executed by the processor, cause the processor to switch the first site to active and to switch the second site to passive upon receipt of an input from the caregiver.

16. The electronic device of claim 14, further comprising instructions which, when executed by the processor, cause the processor to present a warning before switching the second site to active.

\* \* \* \* \*